US006395763B1

(12) United States Patent
Stamos et al.

(10) Patent No.: US 6,395,763 B1
(45) Date of Patent: May 28, 2002

(54) PRODRUGS OF CARBAMATE INHIBITORS OF IMPDH

(75) Inventors: Dean P. Stamos, Framingham; Randy S. Bethiel, Cambridge, both of MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/602,703

(22) Filed: Jun. 23, 2000

Related U.S. Application Data

(60) Provisional application No. 60/141,102, filed on Jun. 25, 1999.

(51) Int. Cl.[7] .................... C07D 263/32; A61K 31/421; C07C 271/00
(52) U.S. Cl. ................. 514/374; 548/236; 514/484; 514/485; 514/482; 514/488; 560/24; 560/27; 560/34; 560/159
(58) Field of Search .................. 548/236; 514/374, 514/484, 485, 482, 488; 560/34, 27, 24, 159

(56) References Cited

U.S. PATENT DOCUMENTS

| | | | | |
|---|---|---|---|---|
| 3,741,959 A | * | 6/1973 | Looker et al. ........... 260/239.1 |
| 4,405,644 A | | 9/1983 | Kabbe et al. ............... 424/322 |
| 4,812,590 A | | 3/1989 | Saari .......................... 860/137 |
| 4,942,226 A | | 7/1990 | Saari ........................... 536/23 |
| 5,495,047 A | | 2/1996 | Van Niel et al. ............ 564/346 |
| 5,534,632 A | | 7/1996 | Or et al. ...................... 540/456 |
| 5,576,313 A | | 11/1996 | Fisher et al. ................ 514/211 |
| 5,807,876 A | | 9/1998 | Armistead et al. .......... 514/374 |
| 6,054,472 A | | 4/2000 | Armistead et al. .......... 514/374 |

OTHER PUBLICATIONS

Beylin, VG et al., "Synthesis of certain 3, 5, 7–disubstituted pyrazolo[3,4–e][1,3]oxazines. Derivatives of a new heterocyclic ring system", *J. Heterocyclic Chemistry*, 1988 25 (1):97–107.

Kahns, AH et al., "N–Acyl derivatives as prodrug forms for amides: chemical stability and enzymic hydrolysis of various N–acyl and N–alkoylcarbonyl amides derivatives", *Chemical Abstracts*, 1991 115:12; abstract No. 57027m.

Saari WS et al., "Cyclization–activated prodrugs. Basic carbamates of 4–hydroxyanisole", *J. Med. Chem.*, 1990 33(1):97–101.

Saari, WS et al., "Cyclization–activated prodrugs. Basic esters of 5–bromo–2'–deoxyuridine", *J. Med. Chem.*, 1990 33(9):2590–5.

Shan D., et al., "Prodrug Strategies Based on Intramolecular Cyclization Reactions", *J. Pharm. Sciences*, 1997 86(7):765–767.

Sharma, SK et al., "Spermexatin and spermexatol: new synthetic spermidine–based siderophore analogues", *J. Med. Chem.*, 1989 32(32):357–67.

\* cited by examiner

*Primary Examiner*—Richard L. Raymond
*Assistant Examiner*—Kahsay Habte
(74) *Attorney, Agent, or Firm*—Fish & Neave; James F. Haley, Jr.; Larry Coury

(57) ABSTRACT

The present invention relates to novel compounds, methods of preparing these compounds, and pharmaceutical compositions comprising these compounds. These compounds are carbamate prodrugs that convert to active inhibitors of the IMPDH enzyme in vivo. The compounds and pharmaceutical compositions of this invention are particularly well suited for activation and subsequent inhibition of the IMPDH enzyme activity. Consequently, these prodrugs may be advantageously used as therapeutic agents for IMPDH mediated processes. This invention also relates to methods for inhibiting the activity of IMPDH using the compounds and compositions of this invention.

14 Claims, No Drawings

PRODRUGS OF CARBAMATE INHIBITORS OF IMPDH

This application claims priority to Ser. No. 60/141,102 filed Jun. 25, 1999.

TECHNICAL FIELD OF THE INVENTION

The present invention relates to novel compounds, methods of preparing these compounds, and pharmaceutical compositions comprising these compounds. These compounds are carbamate prodrugs that convert to active inhibitors of the IMPDH enzyme in vivo. The compounds and pharmaceutical compositions of this invention are particularly well suited for activation and subsequent inhibition of the IMPDH enzyme activity. Consequently, these prodrugs may be advantageously used as therapeutic agents for IMPDH mediated processes. This invention also relates to methods for inhibiting the activity of IMPDH using the compounds and compositions of this invention.

BACKGROUND OF THE INVENTION

IMPDH (EC 1.1.1.205) is an enzyme involved in the de novo synthesis of guanosine nucleotides. The synthesis of nucleotides in organisms, in general, is required for the cells in those organisms to divide and replicate. Nucleotide synthesis in mammals may be achieved through one of two pathways: the de novo synthesis pathway or the salvage pathway. Different cell types use these pathways to different extents. IMPDH catalyzes the NAD-dependent oxidation of inosine-5'-monophosphate (IMP) to xanthosine-5'-monophosphate (XMP)[Jackson R. C. et. al., Nature, 256, pp. 331–333, (1975)].

IMPDH is ubiquitous in eukaryotes, bacteria and protozoa [Y. Natsumeda & S. F. Carr, Ann. N.Y. Acad., 696, pp. 88–93 (1993)]. The prokaryotic forms share 30–40% sequence identity with the human enzyme. Two isoforms of human IMPDH, designated type I and type II, have been identified and sequenced [F. R. Collart and E. Huberman, J. Biol. Chem., 263, pp. 15769–15772, (1988); Y. Natsumeda et. al., J. Biol. Chem., 265, pp. 5292–5295, (1990)]. Each is 514 amino acids, and they share 84% sequence identity.

The de novo synthesis of guanosine nucleotides, and thus the activity of IMPDH, is particularly important in B and T-lymphocytes. These cells depend on the de nova, rather than salvage pathway to generate sufficient levels of nucleotides necessary to initiate a proliferative response to mitogen or antigen [A. C. Allison et. al., Lancet 2(7946), pp. 1179–1183, (1975) and A. C. Allison et. al., Ciba Found. Symp., 48, pp. 207–224, (1977)]. Thus, IMPDH is an attractive target for selectively inhibiting the immune system without also inhibiting the proliferation of other cells.

In addition to its role in the immune response, it is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., Cancer Res., 51, pp. 3886–3890, (1991)]. IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., Transplantation, 59, pp. 655–61 (1995); PCT publication WO 94/12184; and PCT publication Wo 94/01105].

Additionally, IMPDH has been shown to play a role in viral replication in some viral cell lines. [S. F. Carr, J. Biol. Chem., 268, pp. 27286–27290 (1993)]. Analogous to lymphocyte and tumor cell lines, the implication is that the de novo, rather than the salvage, pathway is critical in the process of viral replication.

Mycophenolic acid (MPA) and some of its derivatives have been described as inhibitors of IMPDH [U.S. Pat. Nos. 5,380,879 and 5,444,072 and PCT publications WO 94/01105 and WO 94/12184]. These compounds are potent, non-competitive, reversible inhibitors of human IMPDH type I ($K_i$=33 nM) and type II ($K_i$=9 nM). MPA has been demonstrated to block the response of B and T-cells to mitogen or antigen [A. C. Allison et. al., Ann. N.Y. Acad. Sci., 696, pp. 63–87, (1993)]. MPA is characterized by undesirable pharmacological properties, however, such as gastrointestinal toxicity and poor bioavailability. [L. M. Shaw, et. al., Therapeutic Drug Monitorina, 17, pp. 690–699, (1995)].

Mycophenolate mofetil (MMF), a prodrug which quickly liberates free MPA in vivo, has been approved to prevent acute renal allograft rejection following kidney transplantation. [L. M. Shaw, et. al., Therapeutic Drug Monitoring, 17, pp. 690–699, (1995); H. W. Sollinger, Transplantation, 60, pp. 225–232 (1995)]. Several clinical observations, however, limit the therapeutic potential of this drug. [L. M. Shaw, et. al., Therapeutic Drug Monitoring, 17, pp. 690–699, (1995)]. First, the active drug, MPA, is rapidly metabolized to the inactive glucuronide in vivo. [A. C., Allison and E. M. Eugui, Immunological Reviews, 136, pp. 5–28 (1993)]. The glucuronide then undergoes enterohepatic recycling causing accumulation of MPA in the gastrointestinal tract where it cannot exert its IMPDH inhibitory activity on the immune system. This effectively lowers the drug's in vivo potency, while increasing its undesirable gastrointestinal side effects. In addition, MMF has inherent drawbacks as a prodrug. MMF is the morpholinoethyl ester of MPA. In vivo MMF is deesterified to MPA, but this hydrolysis can occur over a wide pH range in an aqueous environment. Therefore, it is difficult to control the time and location of activation of the drug.

Urea derivatives, which are more effective than MPA as inhibitors of IMPDH, have recently been described in U.S. Pat. No. 5,807,876 and in co-pending continuation applications Ser. No. 08/801,780 and 08/832,165, herein incorporated by reference. These compounds exhibit both an increased overall therapeutic effect and decreased deleterious side effects in their inhibition of IMPDH and in their use as compositions. But the aqueous solubility of these compounds is less than optimum.

The aqueous solubility of an organic molecule can impact its absorption following oral administration. For example, the oral administration of a highly hydrophobic compound can very easily result in poor absorption due to precipitation in the gastrointestinal tract. Formulation of such hydrophobic compounds with surfactants and complexing agents can improve the aqueous solubility of these compounds, but this method becomes more impractical as the aqueous solubility decreases.

However, chemical modification of a drug into a bio- or chemically-reversible prodrug can confer temporary aqueous solubility to the drug substance that allows absorption following oral administration.

For orally administered prodrugs, the drug substance's kinetic solubility in neutral to acidic media is of most interest. In most cases, the kinetic solubility in these media is higher than the corresponding thermodynamic solubility. Therefore, it is advantageous to utilize this transient increase in solubility that immediately follows the conversion of the prodrug to the drug substance. The time it takes to reach thermodynamic equilibrium will vary from compound to compound and can only be determined experimentally. A strategy for creating prodrugs of IMPDH inhibitors that exploits the compound's kinetic solubility would be advantageous. Alternatively, a prodrug which liberates the drug substance as a fine dispersion intestinally may also improve its oral absorption, with smaller particle sizes being preferred.

Prodrug strategies which rely on intramolecular cyclization/transacylation to liberate a drug substance and a lactam derivative have been described where the liberated drugs are alcohols, phenols, and primary and secondary amines. For alcohols [Saari, et al, *J. Med. Chem.*, 33, pp. 2590–2595 (1990)] and phenols [Saari, et al, *J. Med. Chem.*, 33, pp. 97–101 (1990)], the facility of cyclization and hydroxyl liberation is a consequence of the lower $pK_a$ of the resulting leaving group ($pK^a$ 10–16). Such prodrugs are easily prepared by known methods which offer a reasonable amount of synthetic flexibility allowing one to modulate the rate of prodrug to drug conversion. The rates of liberation for cyclizing alcohol and phenol prodrugs are sensitive to pH. For amines [Borchhardt, et al, *Pharm. Sci.*, 86, pp. 765–767 (1997)] strategies have been developed which utilize cyclization of highly constrained systems as well as the use of additional functionalization in the form of aminals. Such measures are taken to overcome the poor ability of alkyl amines to serve as leaving groups ($pK_a \geq 30$). These methods, however, are inadequate for the formation of prodrugs of drugs lacking alcohols, phenols, or primary and secondary amines.

Thus, there is a need for prodrugs of potent IMPDH inhibitors. Desirable properties of these prodrugs would include better aqueous solubility with corresponding improved bioavailability, and the ability to be activated at particular times and locations in the body as needed. Such prodrug inhibitors would have therapeutic potential as immunosuppressants, anti-cancer agents, anti-vascular hyperproliferative agents and anti-viral agents. Specifically, such compounds may be used in the treatment of transplant rejection and autoimmune diseases, such as rheumatoid arthritis, multiple sclerosis, juvenile diabetes, asthma, inflammatory bowel disease, as well as in the treatment of cancer and tumors, such as lymphomas and leukemia, vascular diseases, such as restenosis, and viral replication diseases, such as retroviral diseases and herpes.

SUMMARY OF THE INVENTION

The present invention provides compounds, and pharmaceutically acceptable derivatives thereof, that are prodrugs of carbamate derivatives, described in U.S. Pat. No. 5,807, 876, and in co-pending continuation applications Ser. Nos. 08/801,780 and 08/832,165, that function as inhibitors of IMPDH. The invention further provides a method for preparing pH-triggered, cyclizing prodrugs of drug substances comprising secondary carbamates. The carbamate prodrugs described herein can be selectively activated to produce an active compound and a non-toxic by-product. The release of the active compounds can modulated as a function of pH and rate of liberation, which in turn allows absorption to be more carefully controlled. These compounds can be used a-lone or in combination with other therapeutic or prophylactic agents, such as anti-virals, anti-inflammatory agents, antibiotics, and immunosuppressants for the treatment or prophylaxis of transplant rejection and autoimmune disease. Additionally, these compounds are useful, alone or in combination with other agents, as therapeutic and prophylactic agents for antiviral, anti-tumor, anti-cancer, immunosuppressive chemotherapy and restenosis therapy regimens.

Specifically, the invention provides a compound of the Formula (I):

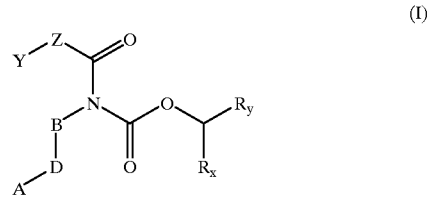

wherein:
A is either B or is selected from:
(C$_1$–C$_6$)-alkyl, or (C$_2$–C$_6$)-alkenyl or alkynyl;
and A optionally comprises up to 2 substituents, wherein:
the first of said substituents, if present, is selected from R$^1$ or B, and
the second of said substituents, if present, is R$^1$; wherein:
each R$^1$ is independently selected from 1,2-methylenedioxy, 1,2-ethylenedioxy, (C$_1$–C$_4$)-alkyl, (C$_2$–C$_4$)-alkenyl or alkynyl, or (CH$_2$)$_n$—W$^1$; wherein n is 0, 1 or 2; R$^1$ is optionally substituted with R$^5$; and
W$^1$ is selected from halogen, CN, NO$_2$, CF$_3$, OCF$_3$, OH, S(C$_1$–C$_4$)-alkyl, SO(C$_1$–C$_4$)-alkyl, SO$_2$(C$_1$–C$_4$)-alkyl, NH$_2$, NH(C$_1$–C$_4$)-alkyl, N((C$_1$–C$_4$)-alkyl)$_2$, N((C$^1$–C$_4$)-alkyl)R$^8$, COOH, C(O)NH2, C(O)NH(C$_1$–C$_4$)-alkyl, C(O)N((C$_1$–C$_4$)-alkyl)$_2$, —C(O)O(C$_1$–C$_4$)-alkyl or O(C$^1$–C$_4$)-alkyl; and
R$^8$ is an amino protecting group;
B is selected from a monocyclic or a bicyclic, saturated or unsaturated or aromatic, ring system consisting of 5 to 6 members per ring, wherein each ring optionally comprises up to 4 heteroatoms selected from N, O, or S, and wherein a CH$_2$ adjacent to any of said N, O, or S heteroatoms is optionally replaced with C(O); and each B optionally comprises up to 3 substituents, wherein:
the first of said substituents, if present, is selected from R$^1$, R$^2$, R$^4$ or R$^5$,
the second of said substituents, if present, is selected from R$^1$ or R$^4$, and
the third of said substituents, if present, is R$^1$; wherein:
each R$^2$ is independently selected from (C$_1$–C$_4$)-alkyl, or (C$_2$–C$_4$)-alkenyl or alkynyl; and each R$^2$ optionally comprises up to 2 substituents, wherein:
the first of said substituents, if present, is selected from R$^1$, R$^4$ and R$^5$, and
the second of said substituents, if present, is R$^1$;
each R$^4$ is independently selected from OR$^5$, OC(O) R$^6$, OC(O)R$^5$, OC(O)OR$^6$, OC(O)OR$^5$, OC(O)N (R$^6$)$_2$, OP(O)(OR$^6$)$_2$, SR$^6$, SR$^5$, S(O)R$^6$, S(O)R$^5$, SO$_2$R$^6$, SO$_2$R$^5$, SO$_2$N(R$^6$)$_2$, SO$_2$NR$^5$R$^6$, SO$_3$R$^6$, C(O)R$^5$, C(O)OR$^5$, C(O)R$^6$, C(O)OR$^6$, NC(O)C (O)R$^6$, NC(O)C(O)R$^5$, NC(O)C(O)OR$^6$, NC(O)C (O)N(R$^6$)$_2$, C(O)N(R$^6$)$_2$, C(O)N(OR$^6$)R$^6$, C(O)N (OR$^6$)R$^5$, C(NOR$^6$)R$^6$, C(NOR$^6$)R$^5$, N(R$^6$)$_2$, NR$^6$C(O)R$^1$, NR$^6$C(O)R$^6$, NR$^6$C(O)R$^5$, NR$^6$C(O) OR$^6$, NR$^6$C(O)OR$^5$, NR$^6$C(O)N(R$^6$)$_2$, NR$^6$C(O)

$NR^5R^6$, $NR^6SO_{2R}6$, $NR^6SO_2R^5$, $NR^6SO_2N(R^6)_2$, $NR^6SO_2NR^5R^6$, $N(OR^6)R^6$, $N(OR^6)R^5$, $OP(O)(OR^6)N(R^6)_2$, and $OP(O)(OR^6)_2$;

each $R^5$ is a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); and each $R^5$ optionally comprises up to 3 substituents, each of which, if present, is selected from 1,2-methylenedioxy, 1,2-ethylenedioxy, $(C_1-C_4)$-alkyl, $(C_2-C_4)$-alkenyl or alkynyl, or $(CH2)_n$—$W^1$; wherein n is 0, 1 or 2;

and wherein any $R^5$ heterocyclic ring in $R^5$ is optionally benzofused;

each $R^6$ is independently selected from H, $(C_1-C_5)$-alkyl, or $(C_2-C_5)$-alkenyl or alkynyl, and each $R^6$ optionally comprises a substituent that is $R^5$; and wherein any carbon atom in any A, $R^2$ or $R^6$ is optionally replaced by O, S, SO, $SO_2$, NH, or $N(C_1-C_4)$-alkyl;

D is selected from $N(R^9)$—C(O)—$N(R^9)$, C(O)—$N(R^9)$, $N(R^9)$—C(O), $NR^9$—C(O)—$C(R^{10})$=$C(R^{10})$;

each $R^9$ is independently selected from hydrogen, $(C_1-C_4)$-alkyl, $(C_2-C_4)$-alkenyl or alkynyl, $R^5$-substituted-$(C_1-C_4)$-alkyl, or $R^5$-substituted-$(C_2-C_4)$-alkenyl or alkynyl; wherein $R^9$ is optionally substituted with up to 3 substituents independently selected from halo, hydroxy, nitro, cyano or amino;

each $R^{10}$ is independently selected from $R^9$, $W^4$—$[C_1-C_4$-alkyl], $W^4$—$[C_2-C_4$-alkenyl or alkynyl], $R^5$-substituted-$[W^4$—$[C_1-C_4$-alkyl$]]$, $R^5$-substituted-$[W^4$—$[C_2-C_4$-alkenyl or alkynyl$]]$, O—$R^5$, $N(R_9)$—$R^5$, S—$R^5$, S(O)—$R^5$, $S(O)_2$—$R^5$, S—C(O)H, $N(R^9)$—C(O)H, or O—C(O)H; wherein:

$W^4$ is O, O—C(O), S, S(O), $S(O)_2$, S—C(O), $N(R^9)$, or $N(R^9)$—C(O); and wherein each $R^{10}$ is optionally and independently substituted with up to 3 substituents independently selected from halo, hydroxy, nitro, cyano or amino;

Z is $C_1-C_{10}$-alkyl, $C_2-C_{10}$-alkenyl or alkynyl, $C_1-C_{10}$ aryl-substituted alkyl, $C_2-C_{10}$ aryl-substituted alkenyl or alkynyl; wherein up to 3 carbons may be replaced with —O—, —S—, —S(O)—, —$S(O)_2$—, —$NR^{14}$; wherein up to 3—CH2— groups may be replaced with —C(O)—; wherein up to 5 hydrogen atoms in any of said alkyl, alkenyl, aryl, or alkynyl are optionally and independently replaced by $R^{13}$ or $R^5$;

$R^{13}$ is halo, —$OR^{14}$, —$N(R^{14})_2$, —$SR^{14}$, —$S(O)R^{14}$, —$S(O)_2R^{14}$, —$S(O)_2OR^{14}$, —$S(O)_2N(R^{14})_2$, —$N(R^{14})S(O)_2N(R^{14})_2$, —$SO(O)_2N(R^{14})_2$, —$NR^{14}C(O)R^{14}$, —$NR^{14}C(O)OR^{14}$, —$N(R^{14})C(O)N(R^{14})_2$, —$N(R^{14})C(S)N(R^{14})_2$, —$N(R^{14})C(NR^{14})N(R_{14})_2$, —$C(O)R^{14}$, —$C(O)OR^{14}$, —$C(O)SR^{14}$, —$C(O)N(R^{14})_2$, —$C(NR^{14})N(R^{14})_2$, —$C(S)OR^{14}$, —$C(S)N(R^{14})_2$, —$N(R^{14})P(O)(OR^{14})_2$, —$OP(O)(OR^{14})_2$;

$R^{14}$ is H, $C_1-C_5$-alkyl, $C_2-C_5$-alkenyl or alkynyl, aryl, or $C_1-C_5$ alkyl-aryl; wherein up to 3 hydrogen atoms in $R^{14}$ are optionally and independently replaced with a substituent that is $R^{13}$; and wherein any $NR^{14}$, taken together with the nitrogen and a carbon adjacent to the nitrogen, optionally forms a 5–7 membered ring, wherein said ring optionally contains up to three additional heteroatoms selected from O, N, S, or $S(O)_2$;

Y is —$NH(R^{14})$;

RX is $(C_1-C_6)$-alkyl, wherein up to 4 hydrogen atoms in said alkyl are optionally and independently replaced by $R^{20}$;

$R^{20}$ is independently selected from halo, —$OR^{21}$, —$N(R_{22})_2$, —$SR^{21}$, —$S(O)R^{21}$, —$S(O)_2R^{21}$, —CN, or;

$R^{21}$ is selected from hydrogen, —$(C_1-C_6)$-straight alkyl, —$(C_1—C_6)$-straight alkyl-$R^5$, —C(O)—$(C_1-C_6)$-alkyl which is optionally substituted with $R^4$, —C(O)—$R^5$, or —$(C_1-C_6)$-straight alkyl—CN;

each $R^{22}$ is independently selected from hydrogen, —$(C_1-C_6)$-alkyl, —$(C_1-C_6)$-alkyl-$R^5$, —$(C_1-C_6)$-straight alkyl-CN, —$(C_1-C_6)$-straight alkyl-OH, —$(C_1-C_6)$-straight alkyl-$OR^{21}$, —C(O)—$(C_1-C_6)$-alkyl, —C(O)—$R^5$, —$S(O)_2$—$(C_1-C_6)$-alkyl, or —$S(O)_2$—$R^5$; or two $R^{22}$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, or S;

$R_Y$ is selected from hydrogen, —$CF_3$, —$(C_1-C_6)$-alkyl, —$(C_1-C_6)$-alkyl—R5, or —$R^5$; or wherein $R_X$ and $R_Y$ are optionally taken together with the carbon atom to which they are bound to form a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); wherein 1 to 4 hydrogen atoms in said ring system are optionally replaced by —$OC(O)CH_3$, —O—$CH_2$—C(O)OH, —O-$CH_2$—C(O)O—$(C_1-C_4)$-alkyl, —O—$CH_2$—CN, or —O—$CH_2$—C≡CH.

The invention also provides compositions comprising the compounds of this invention, as well as multi-component compositions comprising additional IMPDH-inhibitory compounds or prodrugs together with an immunosuppressant. The invention also provides methods of using the compounds of this invention, as well as other related compounds, for the inhibition of IMPDH. Finally, the invention also provides methods for producing carbamate drugs from secondary carbamate prodrugs.

The compounds of this invention, as well as those used in the methods of this invention demonstrate a different metabolic profile than MPA and its derivatives. Because of this difference, methods of this invention and the compounds used therein may offer advantages as therapeutics for IMPDH mediated disease. These advantages include increased overall therapeutic benefit and reduction in deleterious side effects.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Et | ethyl |
| Bn | benzyl |
| DMF | dimethylformamide |
| DMSO | dimethylsulfoxide |
| EtOAc | ethyl acetate |
| IPA | isopropyl alcohol |
| MHz | mega-Hertz |
| NMR | nuclear magnetic resonance |
| TFA | trifluoroacetic acid |
| THF | tetrahydrofuran |

The following terms are employed herein:

Unless expressly stated to the contrary, the terms "—SO$_2$—" and "—S(O)$_2$" as used herein refer to a sulfone or sulfone derivative (i.e., both appended groups linked to the S), and not a sulfinate ester.

The terms "halo" or "halogen" refer to a radical of fluorine, chlorine, bromine or iodine. The terms "immunosuppressant" and "immunosuppression agent" refer to a compound or drug which possesses immune response inhibitory activity. Examples of such agents include cyclosporin A, FK506, rapamycin, leflunomide, deoxyspergualin, prednisone, azathioprine, mycophenolate mofetil, OKT3, ATAG and mizoribine.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "anti-viral agent" refers to a compound or drug capable of preventing infection by or growth of a virus. Examples of such agents include Cytovene, Ganciclovir, trisodium phosphonoformate, Ribavirin, d4T, ddI, AZT, and acyclovir.

The term "anti-vascular hyperproliferative agent" refers to a compound or drug capable of preventing growth of vessels that carry blood or lymph. Examples of such agents include lovastatin, thromboxane A2, synthetase inhibitors, eicosapentanoic acid, ciprostene, trapidil, ACE inhibitors, low molecular weight heparin or 5(3'-pyridinylmethyl) benzofuran-2-carboxylate. "IMPDH-mediated disease" refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as cancer, viral replication diseases and vascular diseases.

The term "treating" as used herein refers to the alleviation of symptoms of a particular disorder in a patient or the improvement of an ascertainable measurement associated with a particular disorder. As used herein, the term "patient" refers to a mammal, including a human.

The term "substituted" refers to the replacement of one or more hydrogen radicals in a given structure with a radical selected from a specified group. When more than one hydrogen radical may be replaced with a substituent selected from the same specified group, the substituents may be either the same or different at every position.

The terms "alkyl", "alkenyl" or "alkynyl" refer to both straight and branched chains unless otherwise specified.

The term "monocyclic or bicyclic, saturated or unsaturated or aromatic, ring system consisting of 5 to 6 members per ring" refers to 5 or 6 member monocyclic rings and 8, 9 and 10 membered bicyclic ring structures, wherein each bond in each ring may be possess any degree of saturation that is chemically feasible. When such structures contain substituents, those substituents may be at any position of the ring system, unless otherwise specified.

As specified, such ring systems may optionally comprise up to 4 heteroatoms selected from N, O or S. Those heteroatoms may replace any carbon atoms in these ring systems as long as the resulting compound is chemically stable.

The term "amino protecting group" refers to a suitable chemical group which may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2 d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

According to one embodiment, the invention provides methods of inhibiting IMPDH activity in a mammal comprising the step of administering to said mammal, a compound of Formula (I):

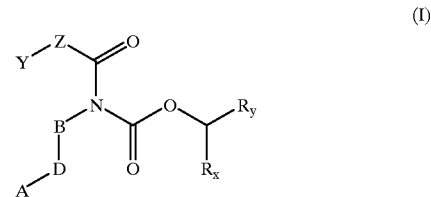

(I)

wherein:
A is either B or is selected from:
(C$_1$–C$_6$)-alkyl, or (C$_2$–C$_6$)-alkenyl or alkynyl; and A optionally comprises up to 2 substituents, wherein:
the first of said substituents, if present, is selected from R$^1$ or B, and
the second of said substituents, if present, is R$^1$; wherein:
each R$^1$ is independently selected from 1,2-methylenedioxy, 1,2-ethylenedioxy, (C$_1$–C$_4$)-alkyl, (C$_2$–C$_4$)-alkenyl or alkynyl, or (CH$_2$)$_n$–W$^1$; wherein n is 0, 1 or 2; R$^1$ is optionally substituted with R$^5$; and
W$^1$ is selected from halogen, CN, NO$_2$, CF$_3$, OCF$_3$, OH, S(C$_1$–C$_4$)-alkyl, SO(C$_1$–C$_4$)-alkyl, SO$_2$ (C$_1$–C$_4$)-alkyl, NH$_2$, NH(C$_1$–C$_4$)-alkyl, N((C$_1$–C$_4$)-alkyl)$_2$, N((C$_1$–C$_4$)-alkyl)R$^8$, COOH, C(O)NH2, C(O)NH(C$_1$–C$_4$)-alkyl, C(O)N ((C$_1$–C$_4$)-alkyl)$_2$, —C(O)O(C$_1$–C$_4$)-alkyl or O(C$_1$–C$_4$)-alkyl; and $R^8$ is an amino protecting group;

B is selected from a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to any of said N, O, or S heteroatoms is optionally replaced with C(O); and each B optionally comprises up to 3 substituents, wherein:

the first of said substituents, if present, is selected from $R^1$, $R^2$, $R^4$ or $R^5$, the second of said substituents, if present, is selected from $R^1$ or $R^4$, and the third of said substituents, if present, is $R^1$; wherein:

each $R^2$ is independently selected from $(C_1–C_4)$-alkyl, or $(C_2–C_4)$-alkenyl or alkynyl; and each $R^2$ optionally comprises up to 2 substituents, wherein:

the first of said substituents, if present, is selected from $R^1$, $R^4$ and $R^5$, and the second of said substituents, if present, is $R^1$;

each $R^4$ is independently selected from $OR^5$, $OC(O)R^6$, $OC(O)R^5$, $OC(O)OR^6$, $OC(O)OR^5$, $OC(O)N(R^6)_2$, $OP(O)(R^6)_2$, $SR^6$, $SR^5$, $S(O)R^6$, $S(O)R^5$, $SO_2R^6$, $SO_2R^5$, $SO_2N(R^6)_2$, $SO_2NR^5R^6$, $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)OR^5$, $NR^6C(O)N(R^6)_2$, $NR^6C(O)NR^5R^6$, $NR^6SO_{2R}6$, $NR^6SO_2R^5$, $NR^6SO_2N(R^6)_2$, $NR^6SO_2NR^5R^6$, $N(OR^6)R^6$, $N(OR^6)R^5$, $OP(O)(OR^6)N(R^6)_2$, and $OP(O)(OR^6)_2$;

each $R^5$ is a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); and each $R^5$ optionally comprises up to 3 substituents, each of which, if present, is selected from 1,2-methylenedioxy, 1,2-ethylenedioxy, $(C_1–C_4)$-alkyl, $(C_2–C_4)$-alkenyl or alkynyl, or $(CH_{2n}—W^1$; wherein n is 0, 1 or 2;

and wherein any $R^5$ heterocyclic ring in $R^5$ is optionally benzofused;

each $R^6$ is independently selected from H, $(C_1–C_5)$-alkyl, or $(C_2–C_5)$-alkenyl or alkynyl, and each $R^6$ optionally comprises a substituent that is $R^5$; and wherein any carbon atom in any A, $R^2$ or $R^6$ is optionally replaced by O, S, SO, $SO_2$, NH, or $N(C_1–C_4)$-alkyl;

D is selected from $N(R^9)$—C(O)—$N(R^9)$, C(O)—$N(R^9)$, $N(R^9)$—C(O), $NR^9$–C(O)—$C(R^{10})$=$C(R^{10})$;

each $R^9$ is independently selected from hydrogen, $(C_1–C_4)$-alkyl, $(C_2–C_4)$-alkenyl or alkynyl, $R^5$-substituted—$(C_1–C_4)$-alkyl, or $R^5$-substituted—$(C_2–C_4)$-alkenyl or alkynyl; wherein $R^9$ is optionally substituted with up to 3 substituents independently selected from halo, hydroxy, nitro, cyano or amino;

each $R^{10}$ is independently selected from $R^9$, $W^4$—$[(C_1–C_4$-alkyl)]$, $W^4$—$C_2–C_4$-alkenyl or alkynyl], $R^5$-substituted-$[W^4—[C_1–C_4$-alkyl]]$, $R^5$-substituted-$[W^4—[C_2–C_4$-alkenyl or alkynyl]]$, O—$R^5$, $N(R^9)$—$R^5$, S—$R^5$, S(O)—$R^5$, $S(O)_2$—$R^5$, S—C(O)H, $N(R^9)$—C(O)H, or O—C(O)H; wherein:

$W^4$ is O, O—C(O), S, S(O), $S(O)_2$, S—C(O), $N(R^9)$, or $N(R^9)$—C(O); and wherein each $R^{10}$ is optionally and independently substituted with up to 3 substituents independently selected from halo, hydroxy, nitro, cyano or amino;

Z is $C_1–C_{10}$-alkyl, $C_2–C_{10}$-alkenyl or alkynyl, $C_1–C_{10}$ aryl-substituted alkyl, $C_2–C_{10}$ aryl-substituted alkenyl or alkynyl; wherein up to 3 carbons may be replaced with —O—, —S—, —S(O)—, —$S(O)_2$—, —$NR^{14}$; wherein up to 3 —CH2— groups may be replaced with —C(O)—; wherein up to 5 hydrogen atoms in any of said alkyl, alkenyl, aryl, or alkynyl are optionally and independently replaced by $R^{13}$ or $R^5$;

$R^{13}$ is halo, —$OR^{14}$, —$N(R^{14})_2$, —$SR^{14}$, —S(O)$R^{14}$, —$S(O)_2R^{14}$, —$S(O)_2OR^{14}$, —$S(O)_2N(R^{14})_2$, —$N(R^{14})S(O)_2N(R^{14})_2$, —$OS(O)_2N(R^{14})_2$, —$NR^{14}C(O)R^{14}$, —$NR^{14}C(O)OR^{14}$, —$N(R^{14})C(O)N(R^{14})_2$, —$N(R^{14})C(S)N(R^{14})_2$, —$N(R^{14})C(NR^{14})N(R^{14})_2$, —C(O)$R^{14}$, —C(O)$OR^{14}$, —C(O)$SR^{14}$, —C(O)N$(R^{14})_2$, —$C(NR^{14})N(R^{14})_2$, —$C(S)OR^{14}$, —$C(S)N(R^{14})_2$, —$N(R^{14})P(O)(OR^{14})_2$, —OP(O)$(OR^{14})_2$;

$R^{14}$ is H, $C_1–C_5$—alkyl, $C_2–C_5$-alkenyl or alkynyl, aryl, or $C_1–C_4$ alkyl-aryl; wherein up to 3 hydrogen atoms in $R^{14}$ are optionally and independently replaced with a substituent that is $R^{13}$; and wherein any $NR^{14}$, taken together with the nitrogen and a carbon adjacent to the nitrogen, optionally forms a 5–7 membered ring, wherein said ring optionally contains up to three additional heteroatoms selected from O, N, S, or $S(O)_2$;

Y is —NH($R^{14}$);

$R_X$ is $(C_1–C_6)$-alkyl, wherein up to 4 hydrogen atoms in said alkyl are optionally and independently replaced by $R^{20}$;

$R^{20}$ is independently selected from halo, —$OR^{21}$, —$N(R_{22})_2$, —$SR^{21}$, —$S(O)R^{21}$, —$S(O)_2R^{21}$, —CN, or;

$R^{21}$ is selected from hydrogen, —$(C_1–C_6)$-straight alkyl, —$(C_1–C_6)$-straight alkyl-$R^5$, —C(O)—$(C_1–C_6)$-alkyl which is optionally substituted with $R^4$, —C(O)—$R^5$, or —$(C_1–C_6)$-straight alkyl—CN;

each $R^{22}$ is independently selected from hydrogen, —$(C_1–C_6)$-alkyl, —$(C_1–C_6)$-alkyl-$R^5$, —$(C_1–C_6)$-straight alkyl—CN, —$(C_1–C_6)$-straight alkyl-OH, —$(C_1–C_6)$-straight alkyl-$OR^{21}$, —C(O)—$(C_1–C_6)$-alkyl, —C(O)—$R^5$, —$S(O)_2$—$(C_1–C_6)$-alkyl, or —$S(O)_2$—$R^5$; or two $R^{22}$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, or S;

$R_Y$ is selected from hydrogen, —$CF_3$, —$(C_1–C_6)$-alkyl, —$(C_1–C_6)$-alkyl-$R^5$, or —$R^5$; or wherein $R_X$ and $R_Y$ are optionally taken together with the carbon atom to which they are bound to form a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); wherein 1 to 4 hydrogen atoms in said ring system are optionally replaced by —OC(O)$CH_3$, —O—$CH_2$—C(O)OH, —O—$CH_2$—C(O)O—($C_1$-$C_4$)-alkyl, —O—$CH_2$—CN, or —O—$CH_2$—C≡CH.

According to one preferred embodiment, $R_X$ and $R_Y$ are taken together with the carbon atom to which they are bound to form a 3-tetrahydrofuranyl moiety that is optionally substituted with —OC(O)$CH_3$, —O—$CH_2$—C(O)OH, —O—$CH_2$—C(O)O—($C_1$-$C_4$) -alkyl, —O—$CH_2$—CN, or —O—$CH_2$—C≡CH.

According to a more preferred embodiment, $R_X$ and $R_Y$ are taken together to form an unsubstituted 3-tetrahydrofuranyl moiety.

According to another preferred embodiment, B is a substituted phenyl group.

According to another preferred embodiment, D is $N(R^9)$—C(O)—$N(R^9)$. According to a more preferred embodiment, $R^9$ is hydrogen.

According to another preferred embodiment, A is a substituted phenyl group and said first substituent is $R^5$.

According to a more preferred embodiment, said $R^5$ substituent is oxazolyl. According to a more preferred embodiment, said second substituent is $R^2$. According to a more preferred-embodiment, said $R^2$ substituent is methoxy. According an even more preferred embodiment $R_X$ and $R_Y$ are taken together to form a 3-tetrahydrofuranyl moiety that is not substituted; B is a substituted phenyl group; and D is NH—C(O)—NH, A is a substituted phenyl group, said first substituent is oxazolyl, and said second substituent is methoxy.

According to another preferred embodiment, Z is $C_2$-$C_6$ straight or branched alkyl or alkenyl; wherein 1 to 2 —$CH_2$— groups are optionally replaced with —C(O)—, —O—, —S—, —S(O)—, or —S(O)$_2$—, and another 1 to 2 —$CH_2$— groups are optionally replaced with —$NR^{14}$; and wherein 1 to 2 hydrogen atoms are optionally replaced with $R^{13}$.

According to a more preferred embodiment, Z is $C_2$-$C_6$ straight or geminally branched alkyl or alkenyl; wherein 1 to 2 —$CH_2$— groups are optionally replaced with —C(O)—; and another 1 to 2 —$CH_2$— groups are optionally replaced with —$NR^{14}$; and wherein 1 hydrogen atom is optionally replaced with C(O)$OR^{14}$; wherein $R^{14}$ is selected from H, $C_1$-$C_5$ straight or branched alkyl, $C_2$-$C_5$ straight or branched alkenyl or alkynyl, aryl, or aryl substituted-$C_1$-$C_5$ alkyl.

According to the most preferred embodiment, the compound has formula (II):

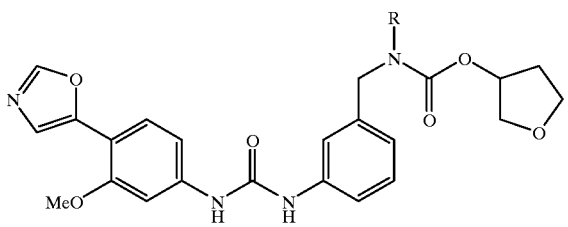

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds of this invention, including the compounds of Formula I, are defined to include derivatives or prodrugs thereof. A "derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of Formula I.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzene-sulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethane-sulfonate, lactate, maleate, malonate, methanesulfonate, 2-naphthalene-sulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N—($C_{14}$ alkyl)$_4^+$ salts.

This invention also envisions the quaternization of any basic nitrogen-containing groups of the compounds disclosed herein. Water or oil-soluble or dispersible products may be obtained by such quaternization.

The compounds of this invention may be synthesized using conventional techniques. Advantageously, these compounds are conveniently synthesized from readily available starting materials. In general, compounds of Formula I are conveniently obtained via methods illustrated in General Synthetic Scheme 3 shown below in the Examples section.

As can be appreciated by the skilled artisan, the synthetic scheme shown is not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are carbamate prodrugs that may be activated to release potent inhibitors of IMPDH. Accordingly, these carbamate prodrug compounds are capable of in vivo activation followed by targeting and inhibition of the IMPDH enzyme. The current strategy for creating a carbamate prodrug is based upon a pH-triggered cyclization event of an acyclic group with a free amine appended directly to the carbamate. At low pH's ($\leq$~4), the amine portion of the prodrug is protonated, water soluble, and stable in an acyclic form. As the pH rises past ~6, a significant amount of the unprotonated amine is present. The unprotonated amine is then capable of cyclizing onto the acyl portion of the molecule with concomitant generation of the carbamate drug and the lactam byproduct (see below for an example). This allows liberation of the active drug and the byproduct in the intestinal tract and takes advantage of the drug's kinetic solubility in the mildly acidic (pH=6–7) environment. The higher kinetic solubility in the intestine may result in improved absorption, thereby increasing the drug's oral bioavailability. Alternatively, the particle size of the precipitated drug substance may be controlled to improve oral absorption, with smaller particle sizes being preferred. Similar approaches have been employed as a prodrug strategy for the formation of lactams from alcohols, but not for the formation of lactams from amines.

In contrast to amines, carbamoylated amines have significantly lowered $pK_a$'s (12–15) and hence offer the possibility of being better leaving groups in a transacylation event. The current cyclizing prodrug stategy allows one to exploit this $pK_a$ difference while maintaining control over the rate of cyclization through the above mentioned synthetic modifications of the cyclizing group. The mechanism of liberation is through intramolecular cyclization of an amine substituted N-acyl side chain of the drug's secondary carbamate (see Scheme 1).

Scheme 1

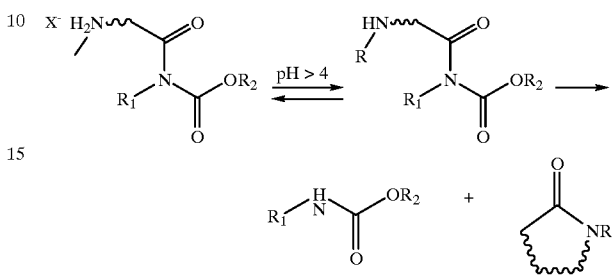

The prodrug can be activated and then absorbed or can be absorbed followed by systemic conversion (pH=7.4) to the drug by the same activating mechanism. It is important to note that the rate of cyclization and liberation of the active drug substance is dependent on the nature of the side chain and the pH of the medium. Functional groups in or on the side chain that impart conformational biases or have advantageous inductive effects can greatly impact the rate of cyclization. This allows for modulation of the chemical behavior of the prodrug (via chemical synthesis) in an effort to optimize the drug's absorption following oral administration.

This approach is shown for several specific compounds in more detail below in Scheme 2.

Scheme 2

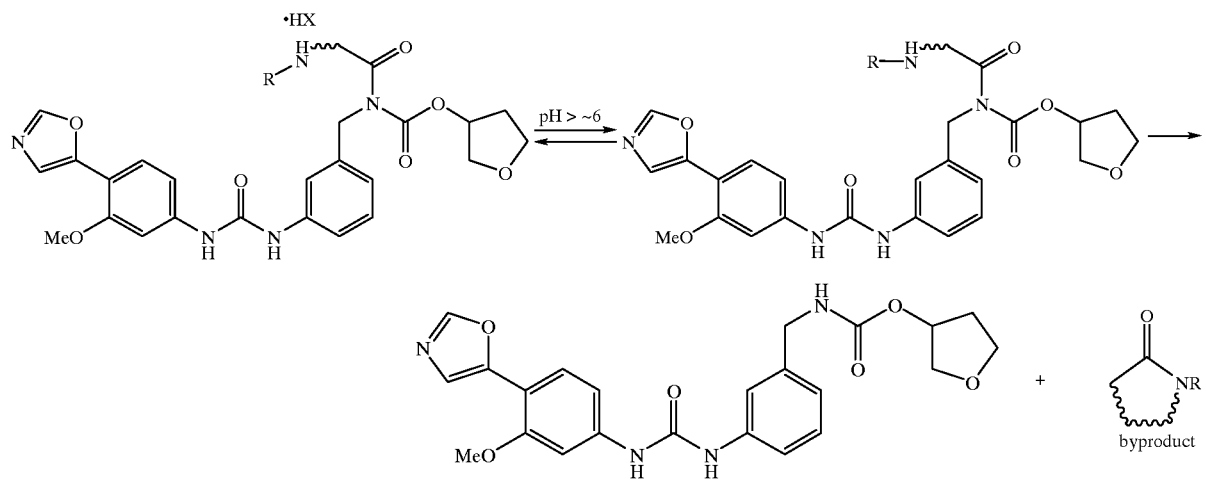

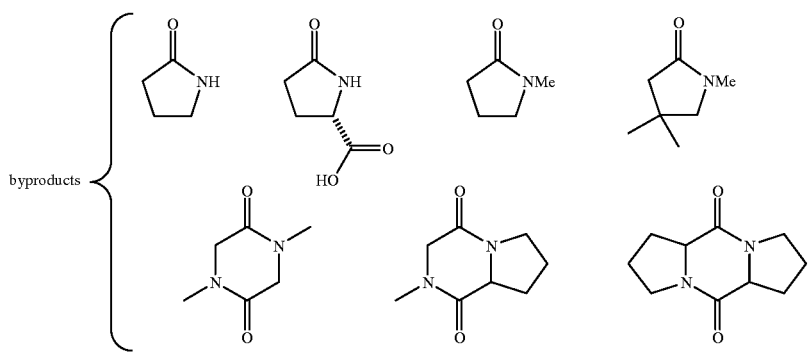

A diverse group of side chains that eventually form the byproducts is needed for two reasons:
1) To influence the rate of cyclization so that both the location in the body and the time at which absorption occurs can be controlled.
2) To allow for the possibility of creating safe, non-toxic byproducts.

Preparation of the requisite N-acyl side chains was accomplished using the novel conditions described in Synthetic Scheme 3 shown in the Examples.

Thus, according to another embodiment, the invention provides a method of forming a carbamate prodrug moiety comprising the steps of:
a) anionically coupling an acyl imidazoyl carbamate with a primary amide or carbamate; and
b) N-alkylating the product of step a).

Activation is monitored by measuring the amounts of the prodrug and the active drug by reverse phase HPLC. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). [See C. Montero et al., *Clinica Chimica Acta*, 238, pp. 169–178 (1995)].

Compositions of this invention comprise a compound of Formula I or a pharmaceutically acceptable salt thereof; and a pharmaceutically acceptable carrier, adjuvant or vehicle. Such composition may optionally comprise an additional agent selected from an immunosuppressant, an anti-cancer agent, an anti-viral agent, or an anti-vascular hyperproliferation compound.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-a-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of Formula I.

The compositions of this invention may be administered orally, parenterally, by inhalation spray, topically, rectally, nasally, buccally, vaginally or via an implanted reservoir. We prefer oral administration or administration by injection. The compositions of this invention may contain any conventional non-toxic carriers, adjuvants or vehicles. In some cases, the pH of the formulation may be adjusted with acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol.

Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is especially useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation. Topically-transdermal patches are also included in this invention.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the IMPDH inhibitory compounds described herein are useful in a monotherapy for the prevention and treatment of IMPDH mediated disease. Typically, the compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an IMPDH inhibitor of Formula I and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen.

According to. one embodiment, the compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG and mizoribine.

According to an alternate embodiment, the compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines and thioxantheres.

According to another alternate embodiment, the compositions of this invention may additionally comprise an anti-viral agent. Examples of anti-viral agents include, but are not limited to, Cytovene, Ganciclovir, trisodium phosphonoformate, Ribavirin, d4T, ddI, AZT, and acyclovir.

According to yet another alternate embodiment, the compositions of this invention may additionally comprise an anti-vascular hyperproliferative agent. Examples of anti-vascular hyperproliferative agents include, but are not limited to, lovastatin, thromboxane A2, synthetase inhibitors, eicosapentanoic acid, ciprostene, trapidil, ACE inhibitors, low molecular weight heparin and 5-(3'-pyridinylmethyl) benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In an alternate embodiment, this invention provides methods of treating or preventing IMPDH mediated disease in a mammal comprising the step of administrating to said mammal any of the compositions and combinations described above. If the composition only comprises the IMPDH inhibitor of this invention as the active component, such methods may additionally comprise the step of administering to said mammal an agent selected from an immunosuppressant, an anti-cancer agent, an anti-viral agent, or an anti-vascular hyperproliferation compound. Such additional agent may be administered to the mammal prior to, concurrently with, or following the administration of the IMPDH inhibitor composition.

In a preferred embodiment, these methods are useful in suppressing an immune response in a mammal. Such methods are useful in treating or preventing diseases, including, transplant rejection and autoimmune diseases, such as rheumatoid arthritis, multiple sclerosis, juvenile diabetes, asthma, and inflammatory bowel disease.

These methods comprise the step of administering to the mammal a composition comprising a compound of any of Formula I and a pharmaceutically acceptable adjuvant. In a preferred embodiment, this particular method comprises the additional step of administering to said mammal a composition comprising an additional immunosuppressant and a pharmaceutically acceptable adjuvant.

Alternatively, this method comprises the step of administering to said mammal a composition comprising a compound of Formula I; an additional immunosuppressive agent and a pharmaceutically acceptable adjuvant.

In an alternate preferred embodiment, these methods are useful for inhibiting viral replication in a mammal. Such methods are useful in treating or preventing, for example, retroviral diseases, such as HTLV-1 and HTLV-2, HIV-1 and HIV-2, and Herpes viruses, such as Epstein-Barr, cytomegaloviruses and Herpes Simplex, Types 1 and 2. [See, U.S. Pat. No. 5,380,879].

These methods comprise the step of administering to the mammal a composition comprising a compound of any of Formula I, and a pharmaceutically acceptable adjuvant. In a preferred embodiment, this particular method comprises the additional step of administering to said mammal a composition comprising an additional anti-viral agent and a pharmaceutically acceptable adjuvant.

Alternatively, this method comprises the step of administering to said mammal a composition comprising a compound of Formula I; an additional anti-viral agent and a pharmaceutically acceptable adjuvant.

In another alternate preferred embodiment, these methods are useful for inhibiting vascular cellular hyperproliferation in a mammal. Such methods are useful in treating or preventing diseases, including, restenosis, and other hyperproliferative vascular disease.

These methods comprise the step of administering to the mammal a composition comprising a compound of any of Formula I, and a pharmaceutically acceptable adjuvant. In a preferred embodiment, this particular method comprises the additional step of administering to said mammal a composition comprising an additional anti-vascular hyperproliferative agent and a pharmaceutically acceptable adjuvant.

Alternatively, this method comprises the step of administering to said mammal a composition comprising a compound of Formula I; an additional anti-vascular hyperproliferative agent and a pharmaceutically acceptable adjuvant.

In another alternate preferred embodiment, these methods are useful for inhibiting tumors and cancer in a mammal. Such methods are useful in treating or preventing diseases, including, tumors and malignancies, such as lymphoma, leukemia and other forms of cancer.

These methods comprise the step of administering to the mammal a composition comprising a compound of any of Formula I, and a pharmaceutically acceptable adjuvant. In a preferred embodiment, this particular method comprises the additional step of administering to said mammal a composition comprising an additional anti-tumor or anti-cancer agent and a pharmaceutically acceptable adjuvant.

Alternatively, this method comprises the step of administering to said mammal a composition comprising a compound of Formula I; an additional anti-tumor or anti-cancer agent and a pharmaceutically acceptable adjuvant.

In order that this invention be more fully understood, the following examples are set forth. These examples are for the purpose of illustration only and are not to be construed as limiting the scope of the invention in any way.

GENERAL MATERIALS AND METHODS

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Analytical HPLC was carried out using a Rainin Mycrosorb-MV, 5m Cyano reverse phase column, 3.9 mm×150 mm, with a flow rate of 1.0 mL/minute and a solvent gradient of 5–100% acetonitrile (0.1% TFA) in water (0.1% TFA). HPLC retention times were recorded in minutes. NMR spectral data was acquired using a Bruker AMX500 in the indicated solvent.

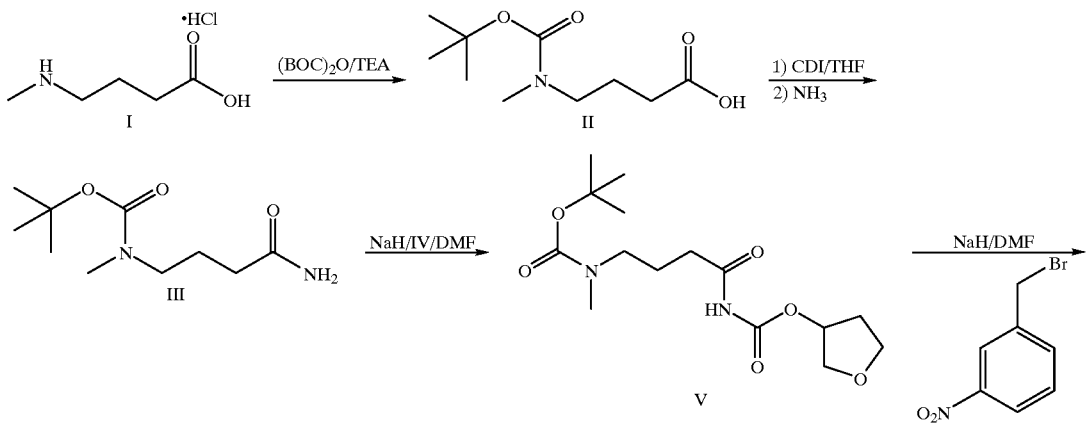

Synthetic Scheme 3: Preparation of prodrug(s)

-continued

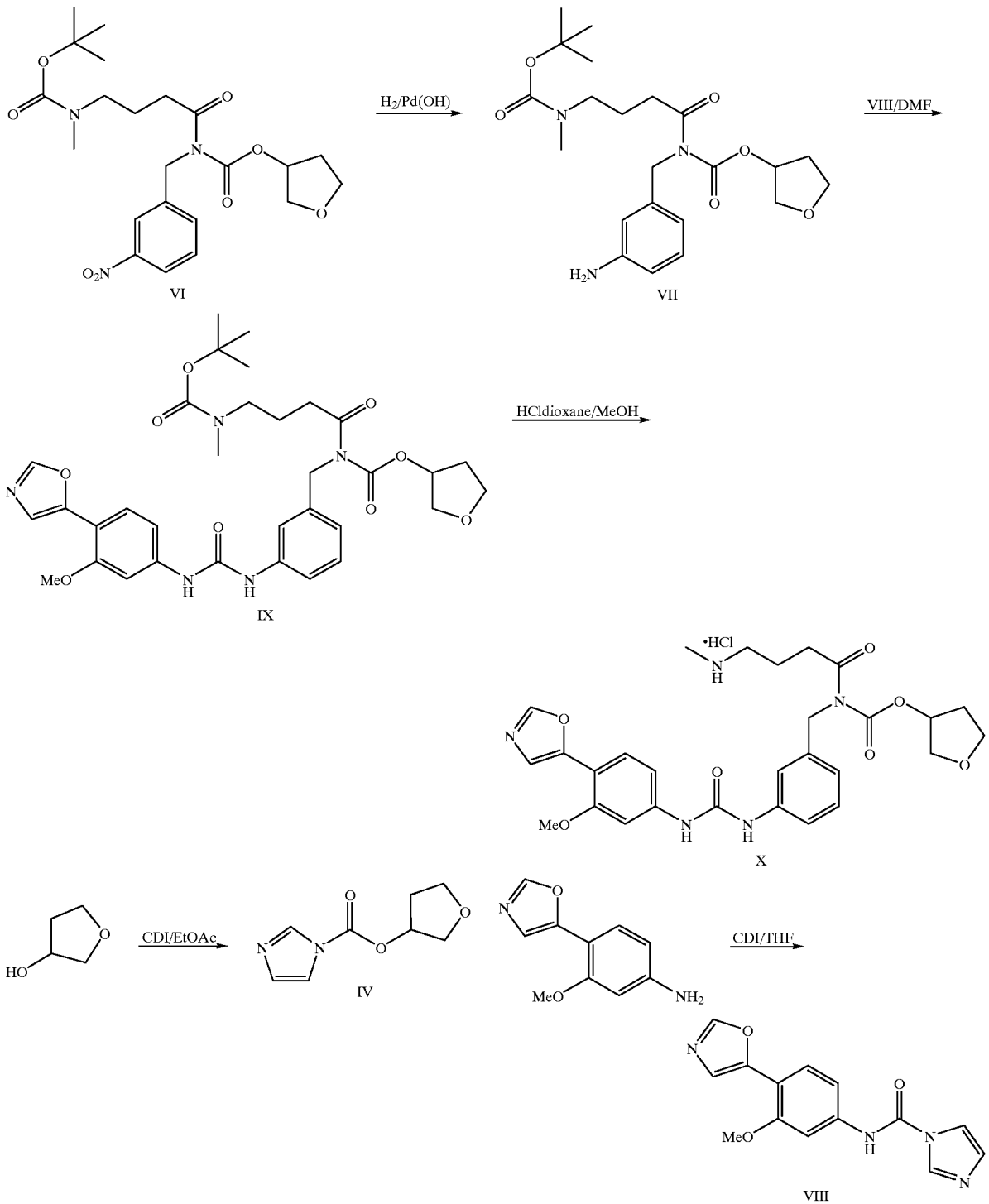

EXPERIMENTALS

II: A stirred, room temperature suspension of 4—(methylamino)butyric acid (I, 15.3 g, 100 mmoles) in a 1/1 (v/v) mixture of isopropanol and acetonitrile (700 mL total volume) was sequentially treated with triethyl amine (28 mL, 200 mmoles) and di-tert-butyl dicarbonate (22 g, 101 mmoles), then stirred overnight at room temperature. The resulting mixture was then concentrated in vacuo, diluted with ethyl acetate, washed twice with aq. $KHSO_4$, once with brine, then dried over $Na_2SO_4$. The crude extracts were filtered and concentrated in vacuo yielding 21.9 g (100%) of II as a brown oil. This product was used without further purification.

1H NMR (500 MHz, dmso-d6): 12.12 (1H, s); 3.21 (2H, s); 2.80 (3H, s); 2.22 (2H, dd); 1.73 (2H, m) 1.43 (9H, s).

III: A stirred, room temperature solution of II (5.5 g, 25.3 mmoles) in $CH_2Cl_2$ (100 mL), under a $N_2$ atmosphere, was treated with carbonyl diimidazole (5.0 g, 30.9 mmoles) in one portion resulting in rapid gas ($CO_2$) evolution. The reaction was stirred at room temperature for 15 min., then treated with a freshly prepared saturated solution of $NH_3$ (excess) in THF. The resulting mixture was gently heated with a heat gun for 5 min., then allowed to cool to room temperature. The crude reaction was diluted with ethyl acetate, washed with aq. $KHSO_4$ twice, then sat. $NaHCO_3$ once, brine once, and dried over $Na_2SO_4$. The crude extract was filtered and concentrated in vacuo to give 4.7 g (86%) of III as an oil. The resulting product was not purified further.

1H NMR (500 MHz, acetone-d6): 6.90 (1H, br. s); 6.30 (1H, br. s); 3.26 (2H, dd); 2.82 (3H, br. s); 2.14 (2H, br. s); 1.78 (2H, m); 1.42 (9H, s).

IV: A stirred, room temperature solution of (S)-3-hydroxy tetrahydrofuran (2.0 mL, 25.04 mmoles) in ethyl acetate (25 mL), under an $N_2$ atmosphere, was treated with carbonyl diimidazole (4.47 g, 27.54 mmoles) in one portion. The resulting mixture was stirred at room temperature for 3 hrs., then directly chromatographed (silica gel, ethyl acetate) to give IV (3.42 g, 75%) as a waxy, white solid. 1H NMR (500 MHz, dmso-d6): 8.32 (1H, s); 7.68 (1H, s); 7.13 (1h, s); 5.56 (1h, m); 4.1–3.75 (4H, m); 2.32 (1H, m); 2.20 (1h, m).

V: A stirred, 0° C. solution of III (13.79 g, 63.76 mmoles) and IV (13.94 g, 76.51 mmoles) in DMF (600 mL), under an $N_2$ atmosphere, was treated with NaH (3.06 g, 76.51 mmoles) in one portion. The reaction was maintained between 0–4° C. for 24 hours then quenched by the addition of sat. $NH_4Cl$ (aq.). The crude mixture was diluted with ethyl acetate and the phases were separated. The organic phase washed twice with sat. $NH_4Cl$, once with brine, dried over $Na_2SO_4$, filtered, and concentrated in vacuo to give a thick oil. The resulting product was not purified further.

1H NMR (500 MHz, acetone-d6): 9.43 (1h, s); 5.24 (1h, m); 3.82 (2H, m); 3.75 (2H, m); 3.25 (2H, br. s); 2.91 (3H, br. s); 2.63 (2H, br. s); 2.17 (1h, m); 1.95 (1h, m); 1.80 (2H, m); 1.43 (9H, s).

VI: A stirred, 0° C. solution of V (63.76 mmoles crude) and 3-nitrobenzyl bromide (14.2 g, 65.74 mmoles) in DMF (500 mL), under an $N_2$ atmosphere, was treated with NaH (2.63 g, 65.74 mmoles) in one portion. The resulting mixture was maintained between 0–4° C. overnight, then quenched by the addition of sat. $NH_4Cl$ (aq.). The crude mixture was diluted with ethyl acetate and the phases were separated. The organic phase washed twice with water, twice with brine, dried over $Na_2SO_4$, filtered, concentrated in vacuo, and purified via chromatography (silica gel, 1/1 ethyl acetate/hexanes) to give VI (19.5 g, 65% over 2-steps) as a clear oil. 1H NMR (500 MHz, acetone-d6): 8.18 (1H, s); 8.13 (1H, d); 7.62 (2H, m); 5.33 (1H, m); 5.08 (2H, s); 3.89–3.63 (4H, m); 3.26 (2H, dd); 2.95 (3H, br. s); 2.81 (2H, br. s); 2.18 (1H, m); 1.99 (1H, m); 1.86 (2H, m); 1.42 (9H, s).

VII: A stirred, room temperature solution of VI (19.5 g, 41.80 mmoles) and $Pd(OH)_2$—C (4 g, 2.09 mmoles) in methanol (400 mL) was flushed with $N_2$ for 15 min., then placed under 1 atmosphere of $H_2$ (balloon) and stirred overnight. Additional $Pd(OH)_2$—C was added (4 g, 2.09 mmoles) and the reaction continued for an additional 4 hrs. The mixture was flushed with $N_2$ for 15 min., filtered through Celite with methanol, then concentrated in vacuo to give VII (17.46 g, 95%) as an oil. The product was not purified further.

1H NMR (500 MHz, dmso-d6): 6.95 (1H, dd); 6.46 (1H, d); 6.41 (1H, s); 6.38 (1H, d); 5.29 (1H, m); 5.08 (2H, s); 4.78 (1H, d); 4.70 (1H, d); 3.90–3.61 (4H, m); 3.23 (2H, m); 2.88 (2H, m); 2.80 (3H, s); 2.12 (1H, m); 1.87 (1H, m); 1.79 (2H, m); 1.43 (9H, s).

VIII: To a stirred, room temperature solution of carbonyl diimidazole (16.3 g, 100 mmoles) was added 3-methoxy-4—(5-oxazolyl)-aniline (19.0 g, 100 mmoles) portionwise over a 15 min. period. The resulting clear, orange solution was warmed to 50° C. for 1 hour, then stirred at room temperature overnight resulting in a heterogeneous mixture. The mixture was filtered, solids washed with fresh THF, and dried in vacuo to give VIII (10.8 g, 38%) as a yellow solid. The combined filtrates were concentrated in vacuo to a thick oil, diluted with $CH_2Cl_2$, then allowed to stand overnight resulting in a second crop (9.0 g, 32%) of the desired product as a yellow powder.

1H NMR (500 MHz, dmso-d6):10.51 (1H, s); 9.04 (1h, s); 8.48 (1h, s); 7.89 (1h, s); 7.78 (1h, d); 7.64 (1H, d); 7.50 (1h, s); 7.47 (1h, s); 7.16 (1H, s); 3.98 (3H, s).

IX: A stirred solution of VII (5.12 g, 11.76 mmoles) and VIII (4.34 g, 15.28 mmoles) in DMF (25 mL), under an $N_2$ atmosphere, was heated to 50° C. overnight. The resulting solution was cooled to room temperature, diluted with ethyl acetate, then treated with enough water to completely precipitate out the dimeric byproduct. The resulting solution was stirred for 15 min., then Celite was added and stirring continued for an additional 20 min. The heterogeneous mixture was filtered through Celite with ethyl acetate, the filtrate washed twice with water, once with brine, dried over $Na_2SO_4$, filtered, concentrated in vacuo, and chromatographed (silica gel, 99/1→98/2→95/5 EtOAc/IPA gradient) to give IX (3.17 g, 41%) as a foamy white solid.

1H NMR (500 MHz, acetone-d6): 8.33 (1h, m); 8.21 (1h, m); 8.11 (1h, s); 7.63 (2H, m); 7.45 (1h, m); 7.44 (1h, s); 7.33 (1h, s); 7.23 (1h, dd); 7.10 (1h, d); 6.95 (1h, m); 5.32 (1h, m); 4.92 (2H, dd); 3.90 (3H, s); 3.89–3.63 (4H, m); 3.29 (2H, m); 2.95 (2H, m); 2.83 (2H, m); 2.81 (3H, s); 2.15 (1h, m); 1.88 (1h, m); 1.42 (9H, s).

X: A stirred, room temperature solution of IX (165 mg, 0.253 mmoles) in dioxane (5 mL) was treated with 4N HCl/dioxane solution (1.0 mL, 4 mmoles) resulting in immediate precipitation of the starting material. The resulting heterogeneous mixture was treated with MeOH (5 mL) and stirred at room temperature for 30 min. providing a clear, homogeneous solution. The mixture was concentrated in vacuo over the weekend to give X (178 mg, quantitative) as a glassy solid.

1H NMR (500 MHz, dmso-d6): 9.63 (1h, s); 9.45 (1h, s); 8.78 (2H, br. s); 8.42 (1h, s); 7.63 (1h, d); 7.53 (1h, s); 7.45 (1h, s); 7.39 (2H, m); 7.25 (1h, ddd); 7.08 (1h, d); 6.87 (1h, d); 5.32 (1h, m); 4.88 (2H, dd); 3.97 (3H, s); 3.90–3.66 (4H, m); 3.05 (2H, m); 2.93 (2H, m); 2.56 (3H, br. s); 2.15 (1h, m); 1.94 (3H, m)

Following the synthesis of the carbamate prodrugs, the structures of various derivatives were determined by their spectral properties. Representative examples of these spectral properties are given below in Table 1.

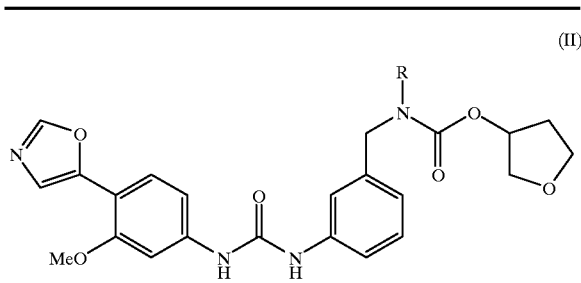

Spectral Data for prodrugs XI–XVII of General Formula II

| compound | R |
|---|---|
| XI | 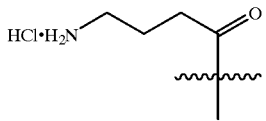 |
| XII | 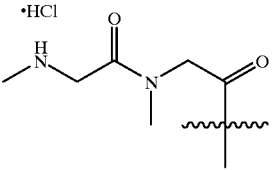 |
| XIII | 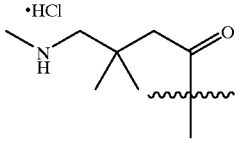 |
| XIV | 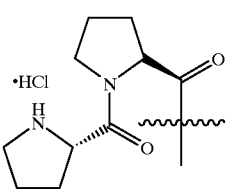 |
| XV | 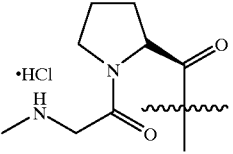 |
| XVI | 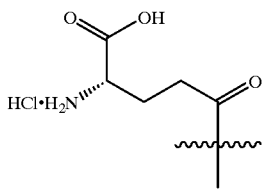 |

-continued

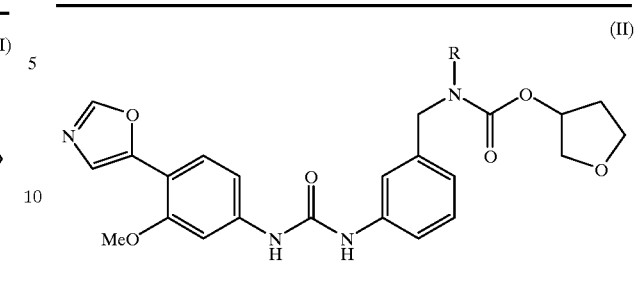

Spectral Data for prodrugs XI–XVII of General Formula II

| compound | R |
|---|---|
| XVII | 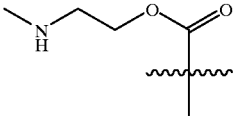 |

XI: 1H NMR (500 MHz, dmso-d6): 9.62 (1H, s); 9.37 (1H, s); 8.43 (1H, s); 7.85 (2H, br. s); 7.65 (1H, d); 7.59 (1H, s); 7.48 (1H, s); 7.37 (2H, m); 7.30 (1H, dd); 7.11 (1H, d); 6.87 (1H, d); 5.31 (1H, m); 4.90 (2H, dd); 3.99 (3H, s); 3.91–3.68 (4H, m); 3.08 (2H, dd); 2.89 (2H, m); 2.21 (1H, m); 2.02 (1H, m); 2.94 (2H, dd).

XII: 1H NMR (500 MHz, dmso-d6): 9.53 (1H, m); 9.41–9.28 (1H, m); 8.88 (2H, m); 8.41 (1H, s); 7.66 (1H, d); 9753 (1H, m); 7.49 (2H, m); 7.41–7.20 (2H, m); 7.10 (1H, d); 6.97–6.81 (1H, m); 5.41–5.26 (1H, m); 4.99–4.70 (3H, m); 4.48–4.00 (3H, m); 3.98 (3H, s); 4.01–3.70 (4H, m); 3.02 (3H, s) 2.61 (3H, s) 2.20 (1h, m); 2.02 (1h, m)

XIII: 1H NMR (500 MHz, dmso-d6): 9.47 (1H, s); 9.25 (1H, s); 8.69–8.31 (2H, m); 8.39 (1h, s); 7.68 (1H, d); 7.52 (1H, s); 8.50 (1H, s); 7.48 (1H, s); 7.31 (1H, d); 7.26 (2H, m); 7.08 (1H, d); 6.87 (1H, d); 5.28 (1H, m); 4.86 (2H, m); 4.19 (3H, br. s); 3.98 (3H, s); 3.88–3.70 (4H, m); 3.10 (2H, dd); 2.60 (2H, s); 2.20 (1H, m); 1.98 (1H, n); 1.12 (6H, s).

XIV: 1H NMR (500 MHz, dmso-d6): 9.41 (1H, m); 9.20 (1H, m); 8.98 (1H, m); 8.64 (1H, m); 8.45 (1H, s); 7.70 (1H, m); 7.55 (1H, s); 7.52 (1H, s); 7.49 (1H, s); 7.30 (2H, m); 7.12 (1H, m); 6.87 (1H, m); 5.67–5.25 (2H, m); 5.04–4.73 (2H, m); 4.58 (1H, m); 4.19–3.49 (6H, m); 3.99 (3H, s); 3.43–3.15 (2H, m); 2.75–1.78 (10H, m).

XV: 1H NMR (500 MHz, dmso-d6): 9.26 (1H, s); 9.07 (1H, s); 8.85 (2H, m); 8.45 (1H, s); 7.69 (1H, d); 7.56 (1H, s); 7.52 (1H, s); 7.49 (1H, s); 7.30 (2H, m); 7.11 (1H, d); 6.88 (1H, d); 5.55–5.47 (1H, m); 5.45–5.26 (1H, m); 5.10–4.76 (2H, m); 4.22–4.02 (3H, m); 3.99 (3H, s); 3.91–3.38 (4H, m); 2.67 (3H, s); 2.36 (1H, m); 2.28–1.80 (6H, m).

XVI: 1H NMR (500 MHz, dmso-d6): 9.53 (1H, s); 9.33 (1H, s); 8.43 (2H, dd); 8.36 (1H, s); 7.59 (1H, d); 7.49 (1H, s); 7.39 (1H, s); 7.39–7.31 (2H, m); 7.21 (1H, dd); 7.04 (1H, d); 6.81 (1H, d); 5.28 (1H, m); 4.82 (2H, ddd); 4.00 (1H, ddd); 3.93 (3H, s); 3.87–3.60 (4H, m); 3.17 (1H, m); 3.09 (1H, m); 2.21–2.02 (3H, m); 1.96 (1H, m).

XVII: 1H NMR (500 MHz, dmso-d6): 9.58 (1H, s); 9.42 (1H, s); 8.90 (2H, br. s); 8.41 (1H, s); 8.62 (1h, d); 7.53 (1h, s); 7.51 (1h, s); 7.43 (1h, s); 7.40 (1h, d); 7.30 (1H, dd); 7.08 (1h, d); 6.92 (1h, d); 5.32 (1H, m); 5.11–4.75 (5H, m); 4.44 (2H, dd); 3.97 (3H, s); 3.89–3.48 (4H, m); 3.30 (2H, m); 2.19 (1h, m); 1.98 (1h, m).

Method for In Vitro $T_{1/2}$ Measurments

200 μcompound were incubated in 100 mM buffer of the desired pH (between 6.5 and 9; 2-[N-morpholino] ethanesulfonic acid was used for pH 6.5, tris [hydroxymethyl]aminomethane was used for pH 7–9) containing 5% dimethyl sulfoxide at room temperature or 37° C. At different time points, 40 μl aliquots were removed and 10 μl of 1 M HCl was added to acidify the reaction and thereby stop the cyclization. Alternatively, an aliquot of the cyclization reaction was injected directly on the HPLC. 10 μl of the quenched or unquenched mixture was injected on a Phenomenex Jupiter C-18 reversed phase HPLC column (2×150 mm), run at 40 ° C., flow rate of 150 μl/min, equilibrated in 95% water/0.1% trifluoroacetic acid, 5% acetonitrile/0.09% trifluoroacetic acid. After 5 min, a 20 min gradient to 100% buffer B was applied and after another 5 min at 100% B the column was re-equilibrated for 10 min. A diode array detector was used and peaks in a plot of the 214 nm signal were integrated. The peak for the active drug was identified by running an authentic standard (the active drug elutes at about 24.5 min). The other prominent peak eluting at 19 to 27 mins, depending on the compound, was integrated as the pro-drug peak. The area of the pro-drug peak was plotted against time and the half life of the pro-drug determined from the plot.

The general reaction for which the $T_{1/2}$ is measured is shown below in Scheme 4.

Scheme 4

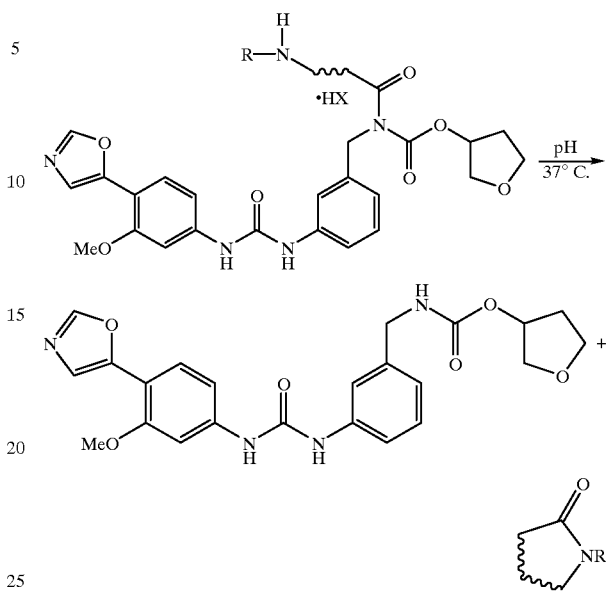

T½ vs. pH results:

| compound | pH = 6.5 | pH = 7.5 | pH = 8.0 | pH = 8.5 | byproduct |
|---|---|---|---|---|---|
| X |  | 230 min. | 75 min. | 15 min. | (N-methyl pyrrolidinone) |
| XI |  |  | 300 min. |  | (pyrrolidinone NH) |
| XII | 10 min. |  |  |  | (dimethyl diketopiperazine) |
| XIII |  | 22 min. |  |  | (dimethyl pyrrolidinone) |

-continued

| compound | pH = 6.5 | pH = 7.5 | pH = 8.0 | pH = 8.5 | byproduct |
|---|---|---|---|---|---|
| XIV | 30 min. | | | | 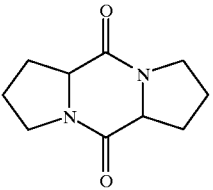 |
| XV | 150 min. | | | | 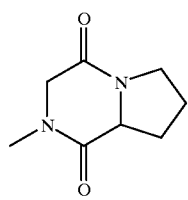 |
| XVI | 240 min. | 60 min. | 10 min. | | 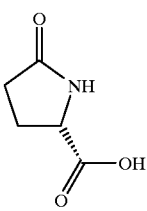 |
| XVII | | | 150 min. | 25 min. | 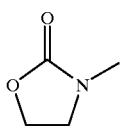 |

Experimental Methods for AUC Determination

Male Sprague Dawley rats were anesthetized with an intramuscular injection of ketamine, xylazine and acepromazine. The carotid artery of each animal was cannulated with PE50 tubing, and in the case of intravenous pharmacokinetic evaluation, the jugular vein was also cannulated with PE50 tubing. The rats were allowed to recover overnight following surgery. Access to food and water was provided ad libitum. After a recovery period of gavage or intravenous bolus. Blood samples were withdrawn at 0 (pre-dose), 0.25, 0.5, 0.75, 1.0, 1.5, 2.0, 3.0, 4.0, 6.0 and 8.0 hours following oral administration or at 0 (pre-dose), 0.08, 0.16, 0.25, 0.5, 0.75, 1.0, 1.5, 2.0, 3.0, 4.0, 6.0 and 8.0 hours). The plasma was separated by centrifugation and the samples were stored frozen at or below −70° C. until HPLC analysis. The HPLC analysis methods were specific for the drug substance that was released from the administered prodrug and the eluent was monitored by ultraviolet methods.

Non-compartmental methods were used to estimate the area under the plasma concentration time curve using the linear trapezoidal rule. The area under the tail was estimated by dividing the last measured concentration by the elimination rate. The elimination rate constant was estimated by log-linear regression of at least the last three measured plasma concentrations. Half-life was estimated from the elimination rate constant (k) as 0.693/k. Oral fraction absorbed was calculated as the percent of the ratio of dose corrected intravenous AUC to the dose corrected oral AUC.

The AUC values for various carbamate prodrugs are summarized in the table below:

Oral Pharmacokinetic (Male Rats) Results of Various Carbamate Prodrugs

| Compound | T1/2 @ 37 ° C. (pH) | AUC* |
|---|---|---|
| X | 230 min. (pH = 7.5) | C |
| XI | 300 min. (pH = 8.0) | C |
| XII | 10 min. (pH = 6.5) | A |
| XIII | 22 min. (pH = 6.5) | A |
| XIV | 30 min. (pH = 6.5) | B |
| XVI | 240 min. (pH = 7.5) | C |

*AUC values:
A: >5 mg.hr/mL
B: 1–5 mg.hr/mL
C: <1 mg.hr/mL

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

What is claimed is:

1. A compound of Formula (I):

(I)

[Chemical structure diagram showing: Y-Z-C(=O)-N(-CH2-B-D-A)(-O-CH(Rx)-O-Ry)]

wherein:
  A is either B or is selected from:
    $(C_1-C_6)$-alkyl, or $(C_2-C_6)$-alkenyl or alkynyl; and
  A optionally comprises up to 2 substituents, wherein:
    the first of said substituents, if present, is selected from $R^1$ or B, and
    the second of said substituents, if present, is $R^1$; wherein:
      each $R^1$ is independently selected from 1,2-methylenedioxy, 1,2-ethylenedioxy, $(C_1-C_4)$-alkyl, $(C_2-C_4)$-alkenyl or alkynyl, or $(CH_2)_n$—$W^1$; wherein n is 0, 1 or 2; $R^1$ is optionally substituted with $R^5$; and
      $W^1$ is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl$)_2$, $N((C_1-C_4)$-alkyl$)R^8$, COOH, $C(O)NH2$, $C(O)NH(C_1-C_4)$-alkyl, $C(O)N((C_1-C_4)$-alkyl$)_2$, —$C(O)O(C_1-C_4)$-alkyl or $O(C_1-C_4)$-alkyl; and
      $R^8$ is an amino protecting group;
  B is selected from a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to any of said N, O, or S heteroatoms is optionally replaced with C(O); and each B optionally comprises up to 3 substituents, wherein:
    the first of said substituents, if present, is selected from $R^1$, $R^2$, $R^4$ or $R^5$,
    the second of said substituents, if present, is selected from $R^1$ or $R^4$, and
    the third of said substituents, if present, is $R^1$; wherein:
      each $R^2$ is independently selected from $(C_1-C_4)$-alkyl, or $(C_2-C_4)$-alkenyl or alkynyl; and each $R^2$ optionally comprises up to 2 substituents, wherein:
        the first of said substituents, if present, is selected from $R^1$, $R^4$ and $R^5$, and
        the second of said substituents, if present, is $R^1$;
      each $R^4$ is independently selected from $OR^5$, $OC(O)R^6$, $OC(O)R^5$, $OC(O)OR^6$, $OC(O)OR^5$, $OC(O)N(R^6)_2$, $OP(O)(OR^6)_2$, $SR^6$, $SR^5$, $S(O)R^6$, $S(O)R^5$, $SO_2R^6$, $SO_2R^5$, $SO_2N(R^6)_2$, $SO_2NR^5R^6$, $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)OR^5$, $NR^6C(O)N(R^6)_2$, $NR^6C(O)NR^5R^6$, $NR^6SO_2R^6$, $NR^6SO_2R^5$, $NR^6SO_2N(R^6)_2$, $NR^6SO_2NR^5R^6$, $N(OR^6)R^6$, $N(OR^6)R^5$, $OP(O)(OR^6)N(R^6)_2$, and $OP(O)(OR^6)_2$;
  each $R^5$ is a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); and each $R^5$ optionally comprises up to 3 substituents, each of which, if present, is selected from 1,2-methylenedioxy, 1,2-ethylenedioxy, $(C_1-C_4)$-alkyl, $(C_2-C_4)$-alkenyl or alkynyl, or $(CH_2)_n$—$W^1$; wherein n is 0, 1 or 2;
  and wherein any $R^5$ heterocyclic ring in $R^5$ is optionally benzofused;
  each $R^6$ is independently selected from H, $(C_1-C_5)$-alkyl, or $(C_2-C_5)$-alkenyl or alkynyl, and each $R^6$ optionally comprises a substituent that is $R^5$; and wherein
  any carbon atom in any A, $R^2$ or $R^6$ is optionally replaced by O, S, SO, $SO_2$, NH, or $N(C_1-C_4)$-alkyl;
  D is selected from $N(R^9)$—C(O)—$N(R^9)$, C(O)—$N(R^9)$, $N(R^9)$—C(O), $NR^9$—C(O)—$C(R^{10})$=$C(R^{10})$;
  each $R^9$ is independently selected from hydrogen, $(C_1-C_4)$-alkyl, $(C_2-C_4)$-alkenyl or alkynyl, $R^5$-substituted-$(C_1-C_4)$-alkyl, or $R^5$-substituted—$(C_2-C_4)$-alkenyl or alkynyl; wherein
  $R^9$ is optionally substituted with up to 3 substituents independently selected from halo, hydroxy, nitro, cyano or amino;
  each $R^{10}$ is independently selected from $R^9$, $W^4$—$[C_1-C_4$-alkyl$]$, $W^4$—$[C_2-C_4$-alkenyl or alkynyl$]$, $R^5$-substituted-$[W^4$—$[C_1-C_4$-alkyl$]]$, $R^5$-substituted-$[W^4$—$[C_2-C_4$-alkenyl or alkynyl$]]$, O—$R^5$, $N(R^9)$—$R^5$, S—$R^5$, S(O)—$R^5$, $S(O)_2$—$R^5$, S—C(O)H, $N(R^9)$—C(O)H, or O—C(O)H; wherein:
    $W^4$ is O, O—C (O), S, S(O), $S(O)_2$, S—C(O), $N(R^9)$, or $N(R^9)$—C(O); and wherein
    each $R^{10}$ is optionally and independently substituted with up to 3 substituents independently selected from halo, hydroxy, nitro, cyano or amino;
  Z is $C_1-C_{10}$-alkylene, $C_2-C_{10}$-alkenyl or alkynyl, $C_1-C_{10}$ aryl-substituted alkylene, $C_2-C_{10}$ aryl-substituted alkenyl or alkynyl; wherein
    up to 3 carbons may be replaced with —O—, —S—, —S(O)—, —$S(O)_2$—, —$NR^{14}$; wherein
    up to 3 —CH2— groups may be replaced with —C(O)—; wherein
    up to 5 hydrogen atoms in any of said alkyl, alkenyl, aryl, or alkynyl are optionally and independently replaced by $R^{13}$ or $R^5$;
    $R^{13}$ is halo, —$OR^{14}$, —$N(R^{14})_2$, —$SR^{14}$, —$S(O)R^{14}$, —$S(O)_2R^{14}$, —$S(O)_2OR^{14}$, —$S(O)_2N(R^{14})_2$, —$N(R^{14})S(O)_2N(R^{14})_2$, —$OS(O)_2N(R^{14})_2$, —$NR^{14}C(O)R^{14}$, —$NR^{14}C(O)OR^{14}$, —$N(R^{14})C(O)N(R^{14})_2$, —$N(R^{14})C(S)N(R^{14})_2$, —$N(R^{14})C(NR^{14})N(R^{14})_2$, —$C(O)R^{14}$, —$C(O)OR^{14}$, —$C(O)SR^{14}$, —$C(O)N(R^{14})_2$, —$C(NR^{14})N(R^{14})_2$, —$C(S)OR^{14}$, —$C(S)N(R^{14})_2$, —$N(R^{14})P(O)(OR^{14})_2$, —$OP(O)(OR^{14})_2$;
    $R^{14}$ is H, $C_1-C_5$-alkyl, $C_2-C_5$-alkenyl or alkynyl, aryl, or $C_1-C_5$ alkyl-aryl; wherein
    up to 3 hydrogen atoms in $R^4$ are optionally and independently replaced with a substituent that is $R^{13}$; and wherein
    any $NR^{14}$, taken together with the nitrogen and a carbon adjacent to the nitrogen, optionally forms a 5–7 membered ring, wherein said ring optionally contains up to three additional heteroatoms selected from O, N, S, or $S(O)_2$;

Y is —NH($R^{14}$);

$R_X$ is ($C_1$–$C_6$)-alkyl, wherein up to 4 hydrogen atoms in said alkyl are optionally and independently replaced by $R^{20}$;

$R^{20}$ is independently selected from halo, —$OR^{21}$, —N($R_{22}$)$_2$, —$SR^{21}$, —S(O)$R^{21}$, —S(O)$_2R^{21}$, —CN, or;

$R^{21}$ is selected from hydrogen, —($C_1$–$C_6$)-straight alkyl, —($C_1$–$C_6$)-straight alkyl-$R^5$, —C(O)—($C_1$–$C_6$)-alkyl which is optionally substituted with $R^4$, —C(O)—$R^5$, or —($C_1$–$C_6$)-straight alkyl-CN;

each $R^{22}$ is independently selected from hydrogen, —($C_1$–$C_6$)-alkyl, —($C_1$–$C_6$)-alkyl-$R^5$, —($C_1$–$C_6$)-straight alkyl-CN, —($C_1$–$C_6$)-straight alkyl-OH, —($C_1$–$C_6$)-straight alkyl-$OR^{21}$, —C(O)—($C_1$–$C_6$)-alkyl, —C(O)—$R^5$, —S(O)$_2$—($C_1$–$C_6$)-alkyl, or —S(O)$_2$—$R^5$; or two $R^{22}$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, or S;

$R_Y$ is selected from hydrogen, —$CF_3$, —($C_1$–$C_6$)-alkyl, —($C_1$–$C_6$)-alkyl-$R^5$, or —$R^5$; or wherein $R_X$ and $R_Y$ are optionally taken together with the carbon atom to which they are bound to form a monocyclic or a bicyclic, saturated or unsaturated or aromatic, ring system consisting of 5 to 6 members per ring, wherein each ring optionally comprises up to 4 heteroatoms selected from N, O, or S, and wherein a $CH_2$ adjacent to said N, O or S maybe replaced with C(O); wherein 1 to 4 hydrogen atoms in said ring system are optionally replaced by —OC(O)$CH_3$, —O—$CH_2$—C(O)OH, —O—$CH_2$—C(O)O—($C_1$–$C_4$)-alkyl, —O—$CH_2$—CN, or —O—$CH_2$—CH=$CH_2$.

2. The compound according to claim 1 wherein $R_X$ and $R_Y$ are taken together to form a 3-tetrahydrofuranyl moiety that is optionally substituted with —OC(O)$CH_3$, —O—$CH_2$—C(O)OH, —O—$CH_2$—C(O)O—($C_1$–$C_4$)-alkyl, —O—$CH_2$—CN, or —O—$CH_2$—CH=$CH_2$.

3. The compound according to claim 2 wherein the tetrahydrofuranyl moiety is not substituted.

4. The compound according to claim 1 wherein B is a substituted phenyl group.

5. The compound according to claim 1 wherein D is N($R^9$)—C(O)—N($R^9$).

6. The compound according to claim 5 wherein $R^9$ is hydrogen.

7. The compound according to claim 1 wherein A is a substituted phenyl group and said first substituent is $R^5$.

8. The compound according to claim 7 wherein $R^5$ is oxazolyl.

9. The compound according to claim 7 wherein said second substituent is $R^2$.

10. The compound according to claim 9 wherein $R^2$ is methoxy.

11. The compound according to claim 1 wherein Z is $C_2$–$C_6$ straight or branched alkyl or alkenyl; wherein 1 to 2 —$CH_2$— groups are optionally replaced with —C(O)—, —O—, —S—, —S(O)—, or —S(O)$_2$—, and another 1 to 2 —$CH_2$— groups are optionally replaced with —$CR^{14}$; and wherein 1 to 2 hydrogen atoms are optionally replaced with $R^{13}$.

12. The compound according to claim 11 wherein Z is $C_2$–$C_6$ straight or geminally branched alkyl or alkenyl; wherein 1 to 2 —$CH_2$— groups are optionally replaced with —C(O)—; and another 1 to 2 —$CH_2$— groups are optionally replaced with —$NR^{14}$; and wherein 1 hydrogen atom is optionally replaced with C(O)$OR^{14}$; wherein $R^{14}$ is selected from H, $C_1$–$C_5$ straight or branched alkyl, $C_2$–$C_5$ straight or branched alkenyl or alkynyl, aryl, or aryl substituted-$C_1$–$C_5$ alkyl.

13. A composition comprising:
   a. a compound according to any one of claims 1–10 in an amount effective to inhibit IMPDH activity following activation of said compound,
   b. a carrier or adjuvant.

14. The composition according to claim 13, wherein said composition is formulated for pharmaceutical administration to a mammal.

* * * * *